United States Patent [19]
White et al.

[11] Patent Number: 6,128,081
[45] Date of Patent: Oct. 3, 2000

[54] METHOD AND SYSTEM FOR MEASURING A PHYSICAL PARAMETER OF AT LEAST ONE LAYER OF A MULTILAYER ARTICLE WITHOUT DAMAGING THE ARTICLE AND SENSOR HEAD FOR USE THEREIN

[75] Inventors: Jeffrey S. White; Frederick P. LaPlant, both of Ann Arbor; John W. Dixon, Ypsilanti, all of Mich.

[73] Assignee: Perceptron, Inc.

[21] Appl. No.: 08/952,556

[22] PCT Filed: Nov. 21, 1997

[86] PCT No.: PCT/US97/21307

§ 371 Date: Nov. 21, 1997

§ 102(e) Date: Nov. 21, 1997

[87] PCT Pub. No.: WO98/22801

PCT Pub. Date: May 28, 1998

Related U.S. Application Data

[60] Provisional application No. 60/031,717, Nov. 22, 1996, and provisional application No. 60/032,006, Nov. 22, 1996.

[51] Int. Cl.$^7$ ................................................ G01B 9/02
[52] U.S. Cl. ............................................ 356/357; 356/432
[58] Field of Search .................................. 356/345, 432, 356/432 T, 357

[56] References Cited

U.S. PATENT DOCUMENTS

| | | |
|---|---|---|
| 3,580,056 | 5/1971 | Warner . |
| 4,379,226 | 4/1983 | Sichling et al. . |
| 4,452,082 | 6/1984 | Miwa . |
| 4,522,510 | 6/1985 | Rosencwaig et al. . |
| 4,625,556 | 12/1986 | Sukahara et al. . |
| 4,659,224 | 4/1987 | Monchalin . |
| 4,704,905 | 11/1987 | Arora . |
| 4,709,357 | 11/1987 | Maki, Jr. . |
| 4,710,030 | 12/1987 | Tauc et al. ........................... 356/432 |
| 5,033,304 | 7/1991 | Rosen . |
| 5,035,144 | 7/1991 | Aussel . |

(List continued on next page.)

FOREIGN PATENT DOCUMENTS

| | | |
|---|---|---|
| 0432 963 A2 | 6/1991 | European Pat. Off. . |
| WO 93/01476 | 1/1993 | WIPO . |

OTHER PUBLICATIONS

Estimating the Parameters of Exponentially Damped Sinusoids and Pole–Zero Modeling in Noise, by Ramdas Kumaresan & Donald W. Tufts, IEEE Transactions on Acoustics, Speech, and Signal Processing, vol. ASP–30, No. 6, Dec. 1982.

*Primary Examiner*—Robert Kim
*Attorney, Agent, or Firm*—Brooks & Kushman PC

[57] ABSTRACT

A method and system are provided to measure a physical parameter of a film such as film thickness or build, in both the wet and dry states of the film, on an article in a production environment without any contact or damage to the film or the rest of the article. The system includes two laser light sources, one pulsed and the other substantially continuous (i.e. long pulses), an interferometer, fiber optic cables, and appropriate optics including multiplexers and demultiplexers to: 1) image and transmit light from both sources to the film on the article; and 2) transmit the light from the continuous source reflected off the film surface back to the interferometer, and a computer containing a data acquisition card to record the data after signal processing and appropriate software to process the data. Light from both light sources are imaged on and over the same spot on the surface of the film. The pulsed light source is used to generate ultrasound in the film. The reflected light from the continuous source is detected by the interferometer to probe the ultrasonic vibrations of the film. The motion of the surface of the film at ultrasonic frequencies generates a Doppler shift in the frequency of the continuous light source. This modulation of the continuous light source frequency is monitored by the interferometer and is converted to a signal which is recorded and processed by the computer. Signal processing involves performing a Z-transform of the data to identify the resonance frequencies of ultrasonic motion in the film. These resonant frequencies, in conjunction with some physical properties of the material of the film are used to determine the film build of the layer.

48 Claims, 7 Drawing Sheets

U.S. PATENT DOCUMENTS

| | | |
|---|---|---|
| 5,137,361 | 8/1992 | Heon et al. . |
| 5,271,274 | 12/1993 | Khuri-Yakub et al. . |
| 5,305,239 | 4/1994 | Kinra . |
| 5,402,235 | 3/1995 | Monchalin . |
| 5,590,090 | 12/1996 | Duggal et al. . |
| 5,604,592 | 2/1997 | Kotidis et al. . |
| 5,615,675 | 4/1997 | O'Donnell et al. . |
| 5,663,502 | 9/1997 | Nagashima et al. . |

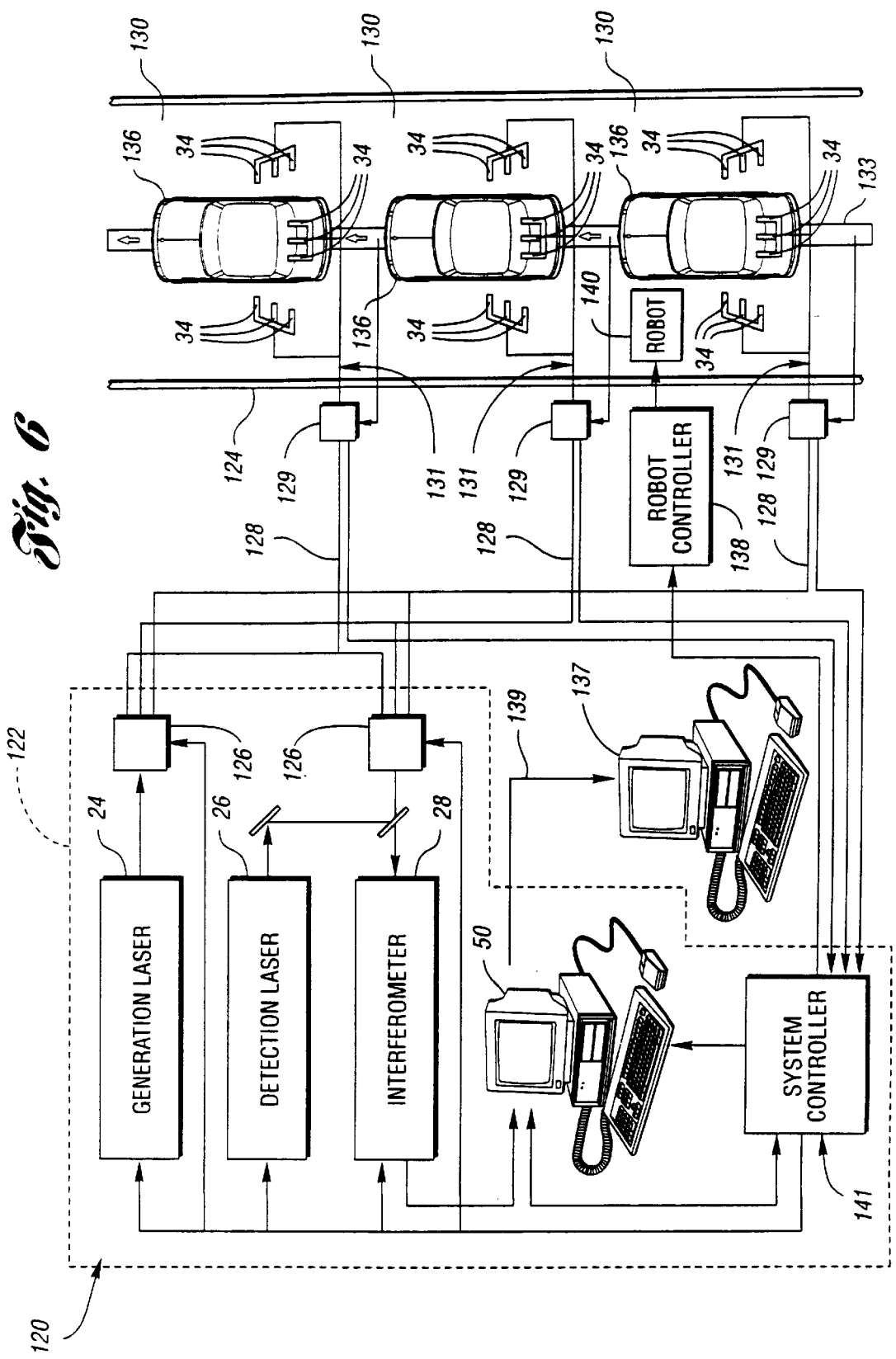

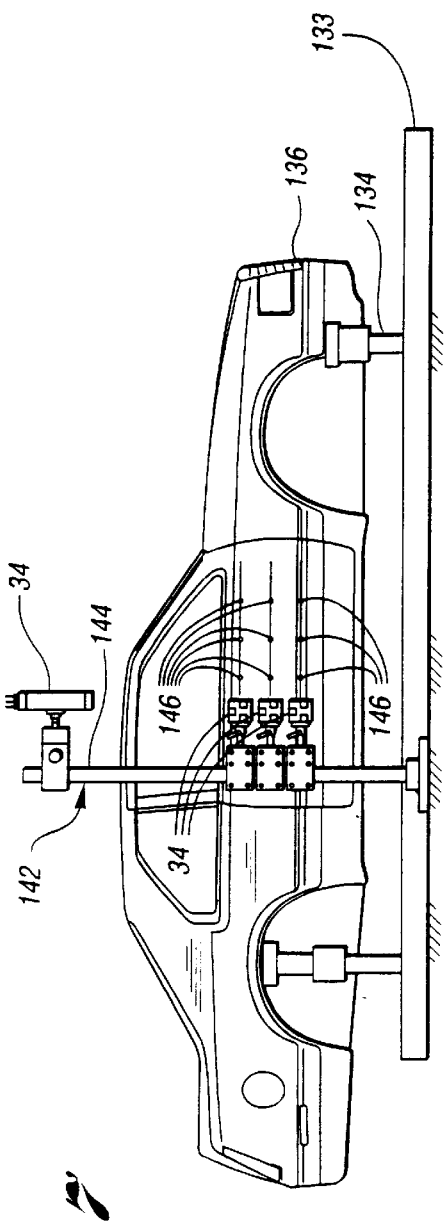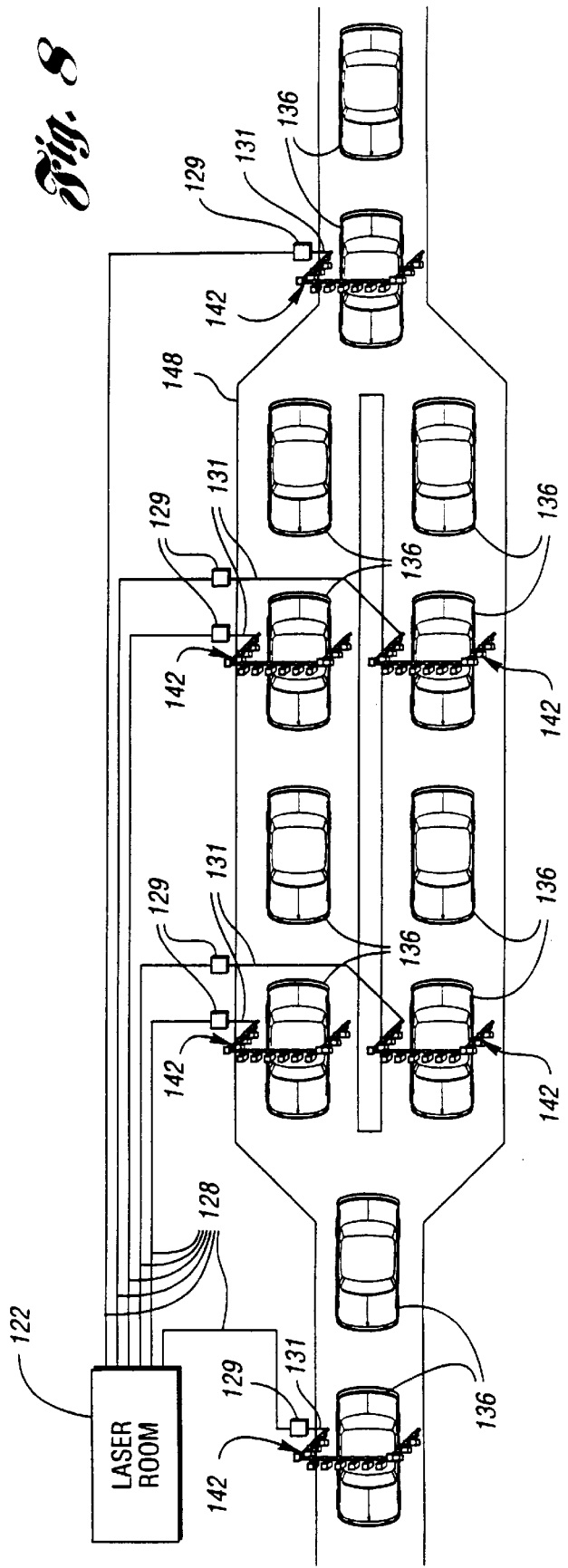

METHOD AND SYSTEM FOR MEASURING A PHYSICAL PARAMETER OF AT LEAST ONE LAYER OF A MULTILAYER ARTICLE WITHOUT DAMAGING THE ARTICLE AND SENSOR HEAD FOR USE THEREIN

This application claims the benefit of Provisional Application Ser. Nos. 60/031,717 and 60/032,006, both filed Nov. 22, 1996.

TECHNICAL FIELD

The present invention relates to methods and systems for measuring a physical parameter of at least one layer of a multilayer article and sensor head for use therein and, in particular, to laser ultrasonic methods and systems for measuring a physical parameter such as thickness of a solid or liquid film formed on an article without damaging the film and a sensor head for use therein.

BACKGROUND ART

In any coating process of an article of manufacture such as an automotive body, there is an optimum specification for the resulting film build, i.e., thickness of the resulting coating layer involving acceptable performance, appearance and materials cost. The ability to measure this film build on-line in a production environment would be beneficial to the manufacturer.

Often, any method for measuring the film build of a coating layer must require that no contact with the film occur either to avoid degrading the effectiveness or marring the appearance of the film.. This is especially true for coatings while they are wet.

With manufacturing film build data, the bulk materials costs can be controlled by applying the minimum amount of material to reach an acceptable film build. Other savings can also be realized, for example measuring and improving the transfer efficiency of the coating process and correlating film build to the quality of the appearance of the final coated surface. An example process and production environment that would benefit from the ability to measure film build on-line is the painting of automobile bodies.

In automated painting operations, a prime concern is the reduction of environmental impacts due to the evaporation of solvents. Means of reducing the amount of solvent released into the atmosphere include electrostatic application of the paint and the use of waterborne paints. Electrostatic application increases the quantity of paint delivered to the painted object, and thus reduces the total quantity of paint required due to the decrease in overspray. The use of waterborne paints dramatically reduces the quantity of solvent utilized in the paint because water is used as a vehicle for paint delivery rather than solvent. Environmental concerns may dictate the exclusive use of waterborne paints in the future.

In order to further reduce waste, thus reducing solvent emissions, and to improve the quality of the finished painted article, it may be necessary to monitor or sense various paint physical parameters such as thickness with precision to effect control.

Waterborne paints are electrically conductive and, therefore, must be isolated from the environment such that an electrostatic charge may be imparted to the flow of paint. This isolation must be at least 100 kilovolts. Further, the painting environment is a hazardous environment due to the few remaining solvents in the paint. Therefore, any device which meters or measures the physical parameters of paint must provide electrostatic isolation and limit energies within the painting environment to less than that required for ignition.

The painting process for automobiles involves applying several coatings of different materials to an underlying metal or plastic substrate 10. As illustrated in FIG. 1, these coatings may include various anticorrosion layers such as a phosphate layer 12, an E-coat layer 14, primer layer(s) 16, colored paint layers 18 (referred to as base coats), and a transparent protective and appearance improving material(s) called a clearcoat 20. The ability to measure both total film build, i.e., the total thickness of all layers and/or the thickness of each individual layer, in both the wet or dry states would be useful.

One non-contact method for measuring solid film thickness and/or other physical properties of the film is provided by ultrasound generation in the film and subsequent ultrasound detection. However, this method typically locally damages or destroys the film.

For example, U.S. Pat. No. 4,659,224 discloses optical interferometric reception of ultrasound energy using a confocal Fabry-Perot interferometer and the detection of the Doppler shift of the laser line frequency as the method to detect the ultrasound.

U.S. Pat. No. 5,137,361 discloses optical detection of a surface motion of an object using a stabilized interferometric cavity. The interferometer cavity is stabilized by controlling the position of the rear cavity mirror with a piezoelectric pusher.

U.S. Pat. No. 5,402,235 discloses imaging of ultrasonic-surface motion by optical multiplexing. Ultrasound is detected using an array of detectors and a "demodulator". The demodulator is typically a photorefractive crystal within which a hologram of the laser beam, both directly from the laser and reflected off the sample's surface, are simultaneously written. The interference between sample laser beam and the beam reflected off the sample surface takes place between the two holographic images generated within the crystal.

U.S. Pat. No. 5,590,090 discloses an ultrasonic detector using vertical cavity surface emitting lasers. The method requires contact between the sample and the equipment.

U.S. Pat. No. 5,035,144 discloses frequency broadband measurement of the characteristics of acoustic waves. Propagating acoustic waves are detected by two different broadband receivers at first and second locations separated by a distance L. The data analysis for this method involves detailed comparisons between group and phase velocities of the data using different amplifiers and narrow band filtering of the signal.

U.S. Pat. No. 5,604,592 discloses a laser ultrasonics-based material analysis system and method using matched filter processing. The system uses a diode laser for detection. Generation and detection of ultrasound is done at different points. The system relies on Time of Flight (TOF) detection which requires generation and detection at separate points since the basis of the measurement is the time it takes for the ultrasonic energy to travel between the two points. The waveshape of the time varying ultrasonic signal is acquired with a matched filter, processed and basically compared to a library of similar signals.

U.S. Pat. No. 5,615,675 discloses a method and system for 3-D acoustic microscopy using short pulse excitation and a 3-D acoustic microscope for use therein.

U.S. Pat. No. 5,305,239 discloses ultrasonic non-destructive evaluation of thin specimens. The method involves data analysis for thin specimens, where "thin" is defined as less than or equal to the wavelength of the inspecting acoustic wave. Analysis is demonstrated with a Fast Fourier Transform (FFT). An important aspect of an FFT is that it can only produce discrete frequency results determined by the number of points taken and data rate used.

SUMMARY OF THE INVENTION

An object of the present invention is to provide a method and system for accurately measuring a physical parameter such as thickness of at least one layer of a multilayer article without damaging the article and sensor head for use therein wherein such measurement can be quickly and safely performed in a factory environment so that the measurement can be used in a real-time, closed loop, feedback control system if desired.

Another object of the present invention is to provide a laser ultrasonic method and system for accurately measuring a physical parameter such as thickness of at least one layer of a multilayer article without damaging the article and sensor head for use therein and which are relatively insensitive to article position and tilt and have a large depth of field.

Still another object of the present invention is to provide a laser ultrasonic method and system for accurately measuring a physical parameter such as thickness of a solid or liquid film formed on a substrate layer without damaging the resulting multilayer article, wherein the system includes a plurality of sensor heads which can operate within a potentially hazardous environment of a paint booth and wherein all light pulses and electrical signals are generated at a central, secure location away from the hazardous environment.

Yet still another object of the present invention is to provide a laser ultrasonic method and system for accurately measuring a physical parameter such as thickness of a liquid film formed on an automotive part without damaging the film, wherein the system includes a plurality of sensor heads and wherein the automotive part moves relative to the sensor heads within a paint booth.

In carrying out the above objects and other objects and features of the present invention, a method is provided for measuring a physical parameter of at least one layer of a multilayer article without damaging the article. The method includes the steps of generating a first pulse of electromagnetic energy, transmitting the first pulse to a sensing station, generating a second pulse of electromagnetic energy, and transmitting the second pulse to the sensing station. The method also includes the step of directing the first pulse at the sensing station toward a first spot on a surface of the article to generate an ultrasonic wave in the article which, in turn, causes ultrasonic motion of the surface of the article without damaging the article. The method further includes the step of directing the second pulse at the sensing station toward a second spot on the surface the article which substantially overlaps the first spot to obtain a reflected pulse of electromagnetic energy which is modulated based on the ultrasonic motion of the surface. Finally, the method includes the steps of transmitting the reflected pulse from the sensing station, detecting the reflected pulse after the step of transmitting the reflected pulse to obtain a corresponding ultrasonic electrical signal, and processing the ultrasonic electrical signal to obtain a physical parameter signal which represents the physical parameter of the at least one layer at the first and second overlapping spots.

Preferably, the step of processing includes the step of initially processing the ultrasonic electrical signal to obtain a resonance frequency signal based on resonance of the at least one layer and then processing the resonance frequency signal to obtain the physical parameter signal.

The multilayer article, such as a vehicle body, may include a metal, plastic or composite material substrate layer. Also, the physical parameter may be thickness of a film layer or the substrate layer or some other physical parameter such as percent solids, density or viscosity of the film layer which may be either a solid film layer or liquid film layer.

Preferably, the steps of generating the pulses and the step of detecting the reflected pulse are performed at a location remote from the sensing station.

Also, preferably, the first and second pulses of electromagnetic energy such as light are substantially collinear at the first and second overlapping spots.

Also, preferably, the step of initially processing the ultrasonic electrical signal includes the steps of digitizing the signal and then applying a Z-transform to the digitized ultrasonic electrical signal.

The sensing station may be located in a hazardous environment and wherein the steps of generating the first and second pulses, the step of detecting the reflected pulse and the step of processing the resultant signal are performed outside of the hazardous environment.

In a production environment, the method further includes the step of moving the article relative to the first and second pulses during the steps of directing the pulses. Also, the method further includes the step of generating a position signal representative of position of the article relative to the first and second directed pulses at the sensing station and wherein the physical property signal is processed with the position signal to locate a defect in the article.

Still, preferably, the method includes the step of generating a control signal based on location of the defect in the article and either controllably moving a surface coating mechanism to a surface coating position in response to the control signal to coat the surface of the article as a function of the location of the defect or using this control signal to adjust some aspect of the original coating equipment (e.g. paint flow controllers) or for some similar method of closed loop feedback control.

Still further in carrying out the above objects and other objects of the present invention, a system is provided for measuring a physical parameter of at least one layer of a multilayer article without damaging the article. The system includes a generation laser for generating a first pulse of electromagnetic energy, a first optical fiber for transmitting the first pulse therethrough to a sensing station, a detection laser for generating a second pulse of electromagnetic energy, and a second optical fiber for transmitting the second pulse therethrough to the sensing station. The system also includes a sensor head coupled to the first and second optical fibers at the sensing station. The sensor head has at least one optical component for directing the first pulse transmitted through the first optical fiber toward a first spot on the surface of the article to generate an ultrasonic wave in the article which, in turn, causes ultrasonic motion of the surface of the article without damaging the article. The sensor head also includes at least one optical component for directing the second pulse toward a second spot on the surface of the article which substantially overlaps the first spot to obtain a reflected pulse of electromagnetic energy which is modulated based on the ultrasonic motion of the surface. The sensor head receives the reflected pulse. The system finally includes an optical detector coupled to the sensor head for detecting the reflected pulse to obtain a corresponding ultrasonic electrical signal, and a signal processor for processing the ultrasonic electrical signal to obtain a physical parameter signal which represents the physical parameter of the at least one layer at the first and second overlapping spots.

Preferably, the optical detector includes an optical interferometer such as a confocal Fabry-Perot type interferometer.

Preferably, the lasers and the optical detector are located remote from the sensing station.

Still further in carrying out the above objects and other objects of the present invention, a sensor head adapted for use in the system is provided. The sensor head includes a housing adapted to receive first and second pulses of electromagnetic energy and a dichroic beam splitter supported within the housing for transmitting one of the pulses and reflecting the other pulse. The sensor head also includes a set of optical components also supported within the housing for (1) directing the first pulse toward a first spot on a surface of the article, (2) directing the second pulse toward a second spot on the surface of the film which substantially overlaps the first spot to obtain a reflected pulse of electromagnetic energy and, finally, (3) receiving the reflected pulse.

Preferably, the beam splitter and the set of optical components are arranged within the housing so that the first and second pulses at the first and second spots are substantially collinear.

Still further in carrying out the above objects and other objects of the present invention in a production environment, a method is provided for measuring a physical parameter of at least one layer over an extended area of a multilayer article without damaging the article. The method includes the steps of generating a first pulse of electromagnetic energy, directing the first pulse into a first plurality of beams, transmitting the first plurality of beams to a plurality of separate locations at a sensing station, generating a second pulse of electromagnetic energy, directing the second pulse into a second plurality of beams, and transmitting the second plurality of beams to the plurality of locations at the sensing station. The method also includes the step of directing the first plurality of beams at the locations at the sensing station toward a first plurality of spots on a surface of the article to generate ultrasonic waves in the article which, in turn, causes ultrasonic motion of the surface of the article without damaging the article. The method also includes the step of directing the second plurality of beams at the sensing station toward a second plurality of spots on the surface the article, each of the second plurality of spots substantially overlapping one of the first plurality of spots to obtain a reflected pulse of electromagnetic energy which is modulated based on the ultrasonic motion of the surface at its respective first and second overlapping spots. Finally, the method includes the steps of transmitting the reflected pulses from the sensing station, collecting the transmitted reflected pulses to obtain collected pulses, detecting the collected pulses to obtain a plurality of corresponding ultrasonic electrical signals, and processing the plurality of ultrasonic electrical signals to obtain a plurality of physical parameter signals which represents the physical property of the at least one layer over the extended area of the article.

Preferably, the method includes the steps of moving the article relative to the sensor station and generating a position signal representative of position of the article at the sensor station and wherein the physical parameter signals are processed with the position signal to locate a defect in the extended area of the article.

Still, preferably, the method further includes the step of generating a control signal based on location of the defect and coating the surface of the article as a function of the control signal.

Yet still further in carrying out the above objects and other objects of the present invention, a system is provided for measuring a physical parameter of at least one layer over an extended area of a multilayer article without damaging the article. The system includes a generation laser for generating a first pulse of electromagnetic energy, a first device for directing the first pulse into a first plurality of beams and a first plurality of optical fibers for transmitting the first plurality of beams therethrough to a corresponding plurality of locations at a sensing station. The system also includes a detection laser for generating a second pulse of electromagnetic energy, a second device for directing the second pulse into a second plurality of beams and a second plurality of optical fibers for transmitting the second plurality of beams therethrough to the corresponding plurality of locations at the sensing station. The system further includes a plurality of sensor heads, each of the sensor heads is positioned at one of the locations at the sensing station and is coupled to one of each of the first and second pluralities of optical fibers. Each of the sensor heads has at least one optical component for directing one of the first plurality of beams toward one of a first plurality of spots on a surface of the article to generate an ultrasonic wave in the article which, in turn, causes ultrasonic motion of the surface of the article without damaging the article. Each of the sensor heads also has at least one optical component for directing one of the second plurality of beams toward one of a second plurality of spots on the surface of the article which substantially overlaps its corresponding spot of the first plurality of spots to obtain a reflected pulse of electromagnetic energy which is modulated based on the ultrasonic motion of the surface at its respective first and second overlapping spots. Each of the sensor heads also receives its reflected pulse. The system still further includes a third device coupled to each of the sensor heads for collecting the reflected pulses to obtain collected pulses, an optical detector coupled to the third device for detecting the collected pulses to obtain a plurality of corresponding ultrasonic electrical signals and a signal processor for processing the plurality of ultrasonic electrical signals to obtain physical parameter signals which represents the physical parameter of the at least one layer over the extended area on the article.

In one embodiment, the system includes a mechanism for moving the article relative to the sensor station and a sensor coupled to the mechanism and the signal processor to generate a position signal representative of position of the article relative to the sensor station and wherein the physical parameter signal is processed with the position signal by the signal processor to locate a defect in the article at the extended area of the article.

Still, preferably, the system includes a controller coupled to the signal processor for generating a control signal based on location of the defect in the article and a surface coating mechanism for coating the surface of the object as a function of the control signal.

In one embodiment, the mechanism includes a robot and the controller is a robot controller.

In one embodiment, the second plurality of optical fibers couple the sensor heads to the third device and in another embodiment a third plurality of optical fibers couple the sensor heads to the third device.

The method and system of the present invention provide numerous advantages. For example, advantages that make the invention most suited for automotive paint film measurements are: 1) the measured parameter is the frequency of the ultrasound and therefore the invention is not affected by changes in the intensity of the signal (intensities are sensitive to a large number of factors (e.g., precise sensor-to-body standoff and orientation, small amounts of overspray build-up on optics) which do not affect this measurement); 2) the measurement is extremely fast (~5 $\mu$s) and thus the measurement is not sensitive to motion or vibrations in the body; 3) the impact of the above two points is that one can use position insensitive sensors (minimal sensor/article alignment is required); 4) the sensors can operate at a large standoff (i.e. 1 meter) from the article; 5) only minimal components (i.e. sensors) required in spray booth or hazardous area; 6) can operate in harsh environments, especially related to temperatures; 7) capable of measuring all materials (composition, wet, dry); and 8) the equipment can be multiplexed (i.e., for example, 400 sensors) thus one set of equipment can cover an entire assembly plant.

The above objects and other objects, features, and advantages of the present invention are readily apparent from the following detailed description of the best mode for carrying out the invention when taken in connection with the accompanying drawings.

BRIEF DESCRIPTION OF THE DRAWINGS

FIG. 6 is a schematic view of a more complex system constructed in accordance with the present invention with generation and detection lasers and an interferometer of the system located in a laser room remote from an automotive paint booth in which sensor heads of the system are located;

FIG. 7 is a schematic side elevational view of an automotive vehicle body carried by a conveyor and a portion of a sensor arch having sensor heads constructed in accordance with the present invention;

FIG. 8 is a schematic top plan view of a plurality of sensor arches positioned at various locations within a paint booth;

BEST MODE FOR CARRYING OUT THE INVENTION

Figure 1:
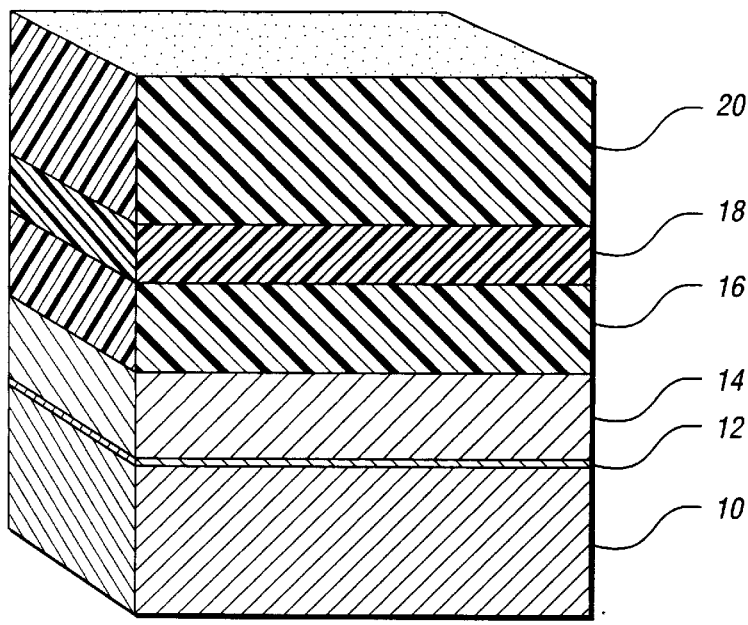
FIG. 1 is a schematic view illustrating a typical automotive coating profile.
Figure 2:
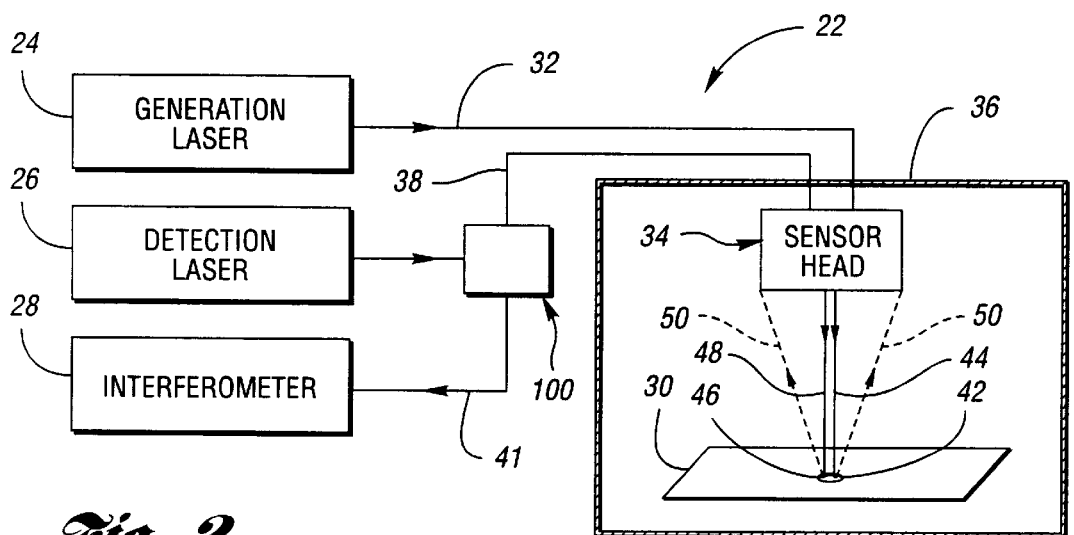
FIG. 2 is a schematic view of a simplified measuring system with a two-fiber laser launch system of FIG. 5 and constructed in accordance with the present invention.

Referring now to FIG. 2, there is illustrated a schematic view of a simplified system constructed in accordance with the present invention, generally indicated at 22. The system includes a generation laser 24, a detection laser 26, and an interferometer 28.

The generation laser 24 produces a very short pulse (~10 ns) that is used to generate the ultrasound in a thin liquid or solid film such as paint formed on the article 30. The generation laser 24 is preferably a Nd:YAG laser with an added fixed OPO having a 1570 nm wavelength which provides <10 mJ/pulse at the measured article. The absorption of this laser's light pulse energy causes a temperature rise in the film (certainly <5° C., probably less than 1° C.) which, in turn, produces an essentially instantaneously generated density gradient in the material. This density gradient produces ultrasound. (This type of ultrasound generation is referred to as thermoelastic generation.) Thus, the short laser pulse is analogous to a quick hammer strike to a bell thereby generating sound.

For wet films, a second method of ultrasound generation is also present. The energy in the pulsed laser 24 is very small, considerably too small to affect the solid materials in the paint, however it will cause an extremely small portion of solvent ($\mu$L) on the film surface to be quickly evaporated. The movement of this solvent mass away from the film produces a force in the opposite direction (i.e., into the film) which is very efficient at generating ultrasound. This ultrasound generation method is referred to as ablative generation, which typically damages the surface of the article inspected. The energies used for this invention will only ablate volatile liquids, not solids, thus no damage occurs to the solid film material.

The detection laser 26 is preferably a Nd:YAG laser having a 1064 or 532 nm wavelength, >2 MHz line-width and provides ≦500 mW of power at the article inspected. The laser 26 is a nominally continuous (wave, or CW) laser which is used to detect the minute motions (<1 nm) of the sample surface due to the ultrasound. The laser 26 can be thought of as producing a very long pulse especially when compared to the length of the pulse produced by the laser 24.

The laser 26 has a very narrow linewidth and thus it is possible to record the ultrasonic surface motions by monitoring the laser frequency as it is Doppler shifted by the ultrasonic motions. The resulting detection laser light pulse reflected off the article 30 is coupled into the interferometer 28 via an optical fiber 41. The interferometer 28 strips away and records the modulations in this laser light pulse line frequency. The frequency of the film resonance is directly related to its thickness, with a thicker film having a slower resonance, again like a bell.

The interferometer 28 is preferably a confocal Fabry-Perot type interferometer constructed generally in accordance with the teachings of the above-noted U.S. Pat. No. 5,137,361.

The system 22 also includes a first optical fiber 32 for transmitting the first pulse generated by the generation laser 24 therethrough to a sensor head, generally indicated at 34, which is shown positioned within a spray booth 36 in which the article 30 is located.

Figure 5:
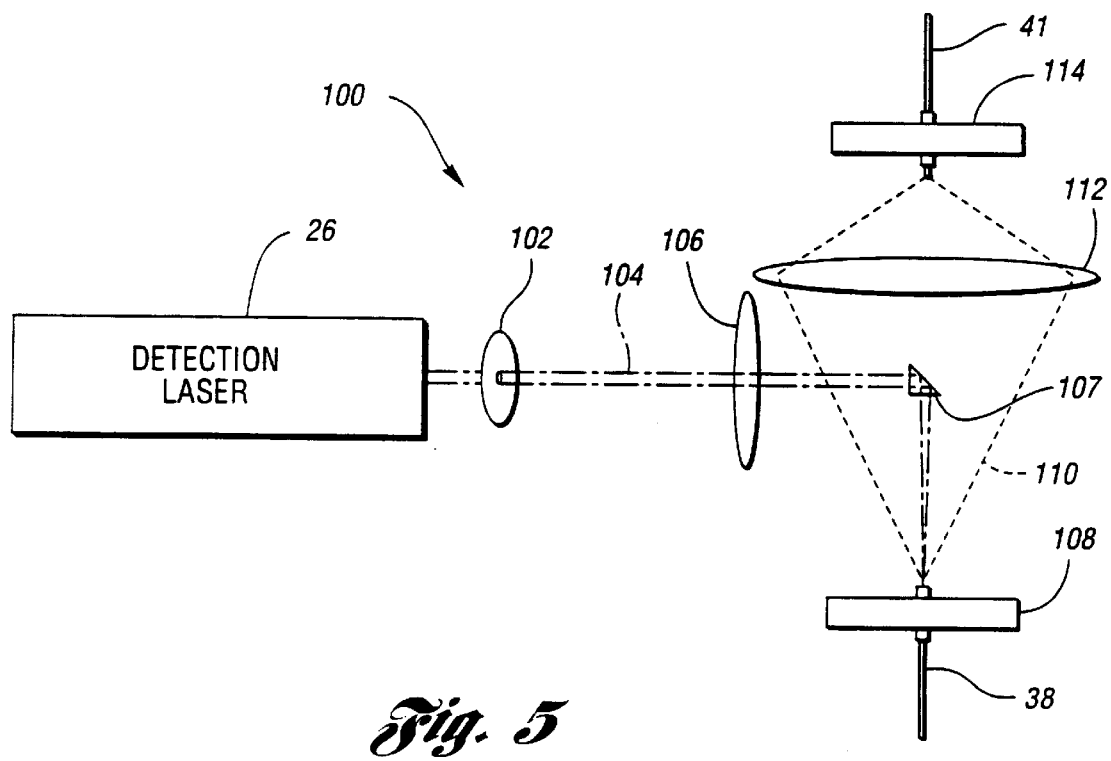
FIG. 5 is a schematic view of a two-fiber laser launch system constructed in accordance with the present invention and utilized in FIG. 2.

The system 22 also includes a second optical fiber 38 for transmitting a second light pulse generated by the detection laser 26 therethrough after striking a reflective element or prism 107 in a system 100 as illustrated in FIG. 5 which directs the second light pulse into the optical fiber 38.

In general, the sensor head 34 directs the first light pulse appearing on the optical fiber 32 at a sensing station within the paint booth 36 toward a first spot 42 along light signal path 44 on a surface of the film of the article 30 to generate an ultrasonic wave such as a longitudinal ultrasonic wave in the film which, in turn, causes ultrasonic motion of the surface of the film without damaging the film or the rest of the article 30.

In general, the sensor head 34 also directs the second pulse of light transmitted through the second optical fiber 38 at the sensing station toward a second spot 46 which is coincident and overlaps the first spot 42 along a light signal path 48 to obtain a reflected pulse of light which returns to the sensor head 34 along a path back to the sensor head. The limits of such a path are indicated at 50 in FIG. 2. The reflected pulse of light is modulated based on the ultrasonic motion of the surface of the film, as is well known in the art.

Referring to FIGS. 2 and 5, the sensor head 34 transmits the reflected pulse of light from the sensing station to the optical fiber 38 and then out of the fiber toward a lens 112 of FIG. 5. This light is coupled into the fiber 41 by the lens 112 therethrough so that it is received by the interferometer 28 along the optical fiber 41. The interferometer 28 detects the reflected pulse of light to obtain a corresponding ultrasonic electrical signal such as the one illustrated in FIG. 9.

A three-fiber system may be used instead of the two-fiber system of FIG. 2 to eliminate the block 100. However, an extra fiber is needed as illustrated at 76 in FIG. 3.

Figure 9:
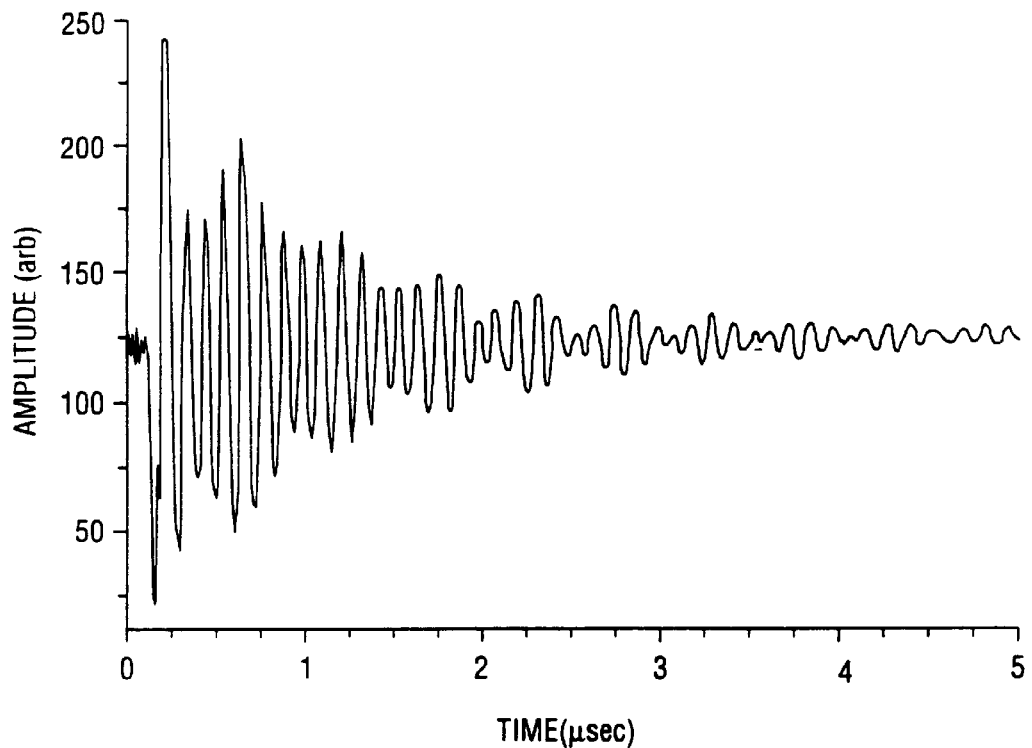
FIG. 9 is a graph illustrating a laser ultrasonic signal obtained from measuring a wet green paint on a 1.0 mil E-Coat with a 1.6 mil primer.
Figure 10:
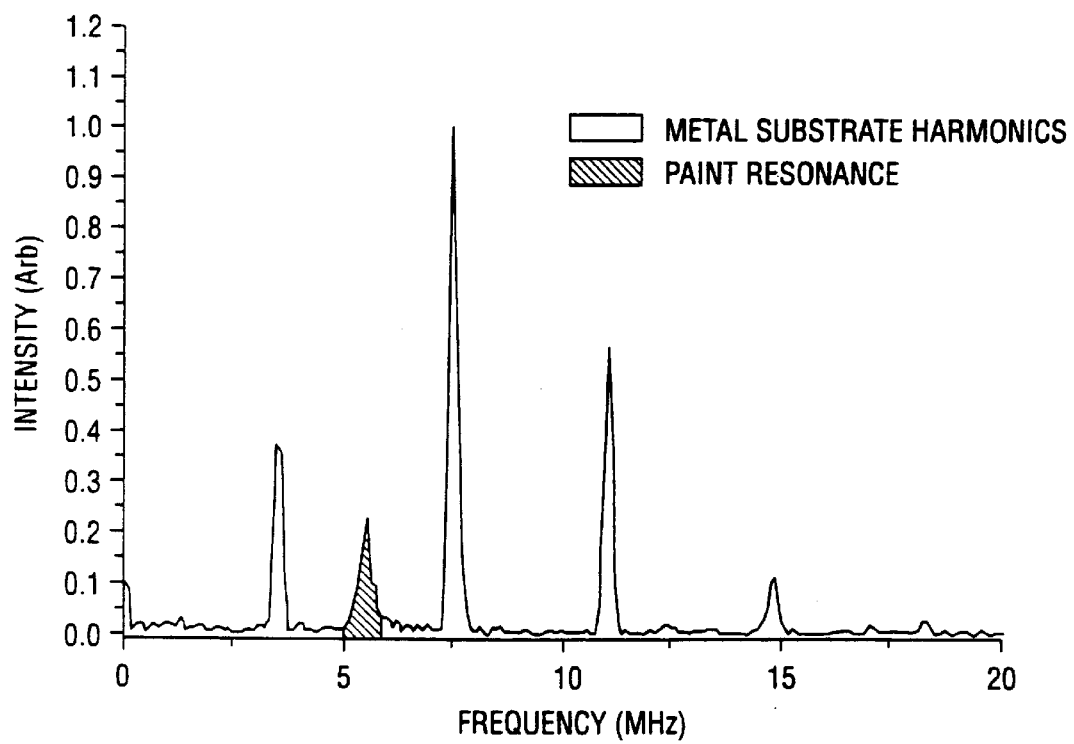
FIG. 10 is a graph of the signal of FIG. 9 after transformed by a discrete Fourier transform and which illustrates resonance frequencies of the substrate and a paint film.

As illustrated in the embodiment of FIG. 6, the interferometer 28 is coupled to a computer 50 to process the ultrasonic electrical signal provided by the interferometer 28 to obtain a physical property signal such as a thickness signal which represents the thickness of the film or substrate of the multilayer article 30. In general, the computer 50 is programmed to initially digitize the ultrasonic electrical signal to obtain a discrete-time signal and then, by applying a Z-transform thereto, to obtain the resonance frequencies in the ultrasonic signal. The resonant frequencies obtained from the ultrasonic signal in FIG. 9 are illustrated in FIG. 10. These frequencies in FIG. 10 were obtained by a Fourier transform as opposed to a Z-transform for this illustrative example due only to the ease of graphing the output of a Fourier transform. The actual method to extract the resonant frequencies is with a Z-transform and then the computer 50 processes the resonance frequencies to obtain the thickness signal as described in greater detail hereinbelow.

Figure 3:
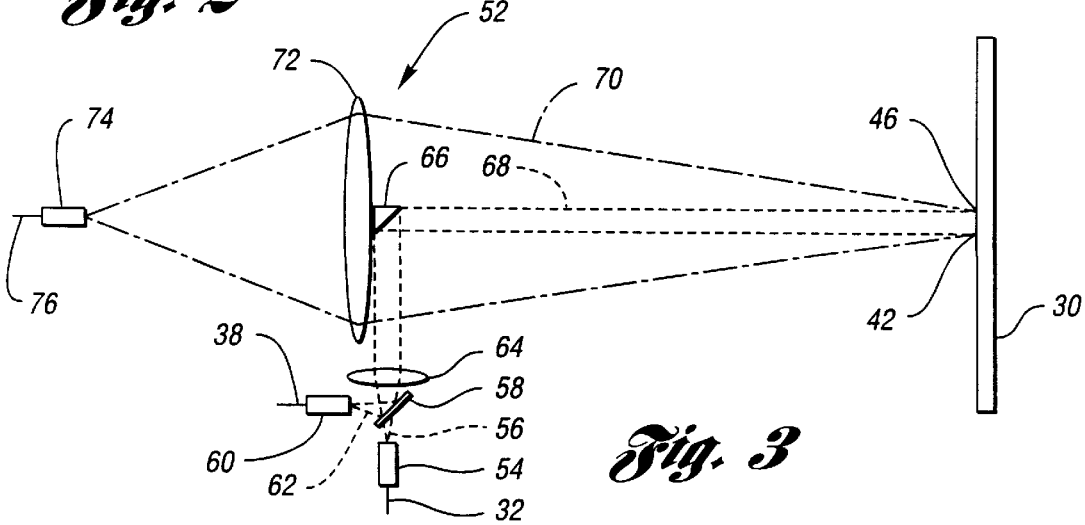
FIG. 3 is a schematic view of a three-fiber sensor head constructed in accordance with the present invention without its housing.

Referring now to FIG. 3, there is illustrated one embodiment of a sensor head, generally indicated at 52 and constructed in accordance with the present invention. The sensor head 52 typically includes a support housing (which housing is not shown in FIG. 3 for simplicity). The sensor head 52 receives the first pulse of light from a coupler 54 formed on one end of the fiber 32 to provide an optical signal 56 which is transmitted through a dichroic beam splitter 58.

The sensor head 52 also supports a coupler 60 which couples the optical fiber 38 to the sensor head 52 to transmit a laser light signal 62 to the beam splitter 58 which reflects the second pulse of light. A lens 64 focuses the first and second pulses of light to a prism or mirror 66 which, in turn, reflects the first and second pulses of light along light signal path 68 to the spots 42 and 46 on the article 30. Thus, the first and second pulses of light are directed toward the article collinearly.

The resulting reflected pulse of light travels along any path within the limits set by path 70 to a lens 72 which, in turn, focuses the reflected pulse of light to a coupler 74. The coupler 74 is coupled to a collection fiber 76 which returns the reflected pulse of light to the interferometer 28 thereby eliminating the necessity of having the system 100.

Figure 4:
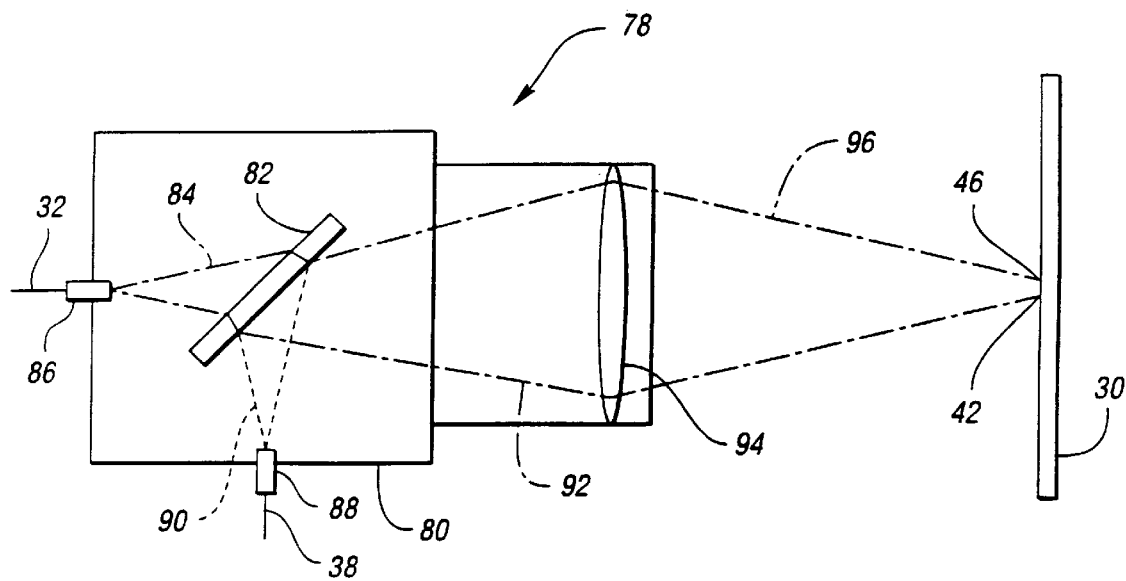
FIG. 4 is a schematic view of a two-fiber sensor head constructed in accordance with the present invention.

Referring now to FIG. 4, there is illustrated a second embodiment of a sensor head, generally indicated at 78. The sensor head 78 may be utilized in the system 22 since optical fiber 38 serves not only as a delivery fiber but also as a collection fiber.

The sensor head 78 includes a housing 80 for housing optical components of the sensor head therein. A typical standoff between the housing 80 and the article 30 is 150 mm but can be widely varied. The sensor head 78 includes a dichroic beam splitter 82 supported within the housing 80 to transmit the first pulse of light generated by the generation laser 24 appearing along path 84 as emitted from a coupler 86 which couples the optical fiber 32 to the housing 80 of the sensor head 78.

The beam splitter 82 also reflects the second pulse of light from the optical fiber 38 through a coupler 88 along a path 90 so that the resulting first and second pulses of light are collinear within the sensor head 78 along a path 92 within the housing 80.

The sensor head 78 also includes a lens 94 for imaging the first and second pulses of light along a path 96 to the spots 42 and 46, respectively, on the film layer of the article 30. In turn, a reflected pulse of light travels along any path within the limits set by path 96 through the lens 94, travels along any path within the limits set by path 92, is reflected by the beam splitter 82 to travel along any path within the limits set by the path 90 back to the coupler 88 and back through the optical fiber 38 to the optical system 100 and to the interferometer 28 through the fiber 41.

Referring again to FIG. 5, there is illustrated a schematic view of a two-fiber laser launch system for the second pulse of light source. In general, the laser launch system 100 illustrates in detail how the second pulse of light is transmitted to the optical fiber 38 as well as how the reflected pulse of light is transmitted from the optical fiber 38 to the optical fiber 41 and then to the interferometer 28.

The system 100 includes a shutter 102 which allows a portion of the second pulse of light to pass therethrough along a path 104 to a focusing lens 106 which focuses the second pulse of light to a mirror or prism 107 which, in turn, directs the second pulse of light to a coupler 108 which couples the second pulse of light to the optical fiber 38.

The reflected pulse of light is transmitted by the optical fiber 38 to the coupler 108 and, after being emitted therefrom, travels along the path 110 to the condenser lens 112 for focusing to the optical fiber 41 by means of a coupler 114.

Referring now to FIG. 6, there is illustrated a more complex system, generally indicated at 120, also constructed in accordance with the present invention. The generation laser 24, the detection laser 26 and the interferometer 28 of the system are located in a laser room 122 which is remote from a paint booth 124 in which a plurality of sensor heads, such as the sensor head 34, are located at a plurality of sensor stations 130.

The system 120 includes multiplexing and demultiplexing elements 126 for multiplexing or directing the first and second pulses of light generated by the generation laser 24 and the detection laser 26 into first and second pluralities of beams of light and for demultiplexing or collecting the reflected pulses of light for detection by the interferometer 28. Optical fiber bundles 128 extend between the room 122 and local controllers 129 located near the paint booth 124 adjacent their respective sensor stations 130. The fiber bundles 128 provide paths for the first and second plurality of beams of coherent light and the reflected pulses of light between the two areas. Each local controller 129 includes a computer for controlling multiplexing elements (not shown) for multiplexing or directing the first and second pulses of light generated by the generation laser 24 and the detection laser 26 and demultiplexers (not shown) for demultiplexing or collecting the reflected light pulses for ultimate use by the interferometer 28.

In this manner, only a few number of optical fibers need be connected between the laser room 122 and the local controllers 129 which typically will be widely separated. A larger number of optical fibers 131 which extend from the local controllers 129 to the plurality of sensor heads, such as sensor head 34, are of a much shorter length, thus reducing the total amount of optical fiber required. In systems with a few number of sensor heads, the local controller multiplexer can be omitted.

In the embodiment of FIG. 6, multiplexing is utilized to take multiple measurements with the above components. Multiplexing both light sources 24 and 26 and the reflected light pulses from the car body surfaces couple the light beams into the fiber optic cables 128. The light sources 24 and 26 and the interferometer 28 are located remotely from automotive body assemblies 136.

With the use of acousto-optic (AO) cells and/or reflective optics on galvanometers and/or translating fiber optical switches (or any form of optical switches), pulses from the light sources 24 and 26 can be directed into a specified fiber of a large set of fibers. In conjunction with directing pulses from the light sources 24 and 26 into different fibers, the output from the fiber which collects the reflected light from the film surface is directed to the interferometer 28 for recording and processing.

The sensor heads 34 are positioned to make measurements at the desired multiple remote positions at the sensor stations 130. The second light source 26 and the light reflected from the film of the article are either carried on separate fibers or combined into a single fiber with a beam splitter or similar optic.

In this manner, the film build measurement of many different positions with the same light sources and interferometer is achieved.

As illustrated in FIGS. 6 and 8, the article may be an automotive assembly 136 of metal parts which moves relative to arches 142 of sensor heads 34 of the system. In such a system, position signals generated by an encoder and limit switches (not specifically shown but located within the spray booth) coupled to the moving assembly 136 through a carriage 134 and connected to the local controllers 129 are processed together with the measurements at the computer 50 to locate those areas of the film which are either too thin or too thick.

The method and system may be utilized with a robot controller 138 which controls a robot 140 to spray coat a surface of the assembly 136 at the location of the thin film. Another method would utilize the thickness signals as a closed loop feedback control to adjust some parameter(s) (e.g. paint flow control) of the process.

In the example illustrated in FIG. 6, each optical fiber bundle 128 preferably includes two optical fibers to service each local controller 129. Each optical fiber bundle 131 preferably includes eighteen optical fibers to service the nine total sensor heads 34 positioned at each sensing station 130 within the paint booth 124.

The computer 50 operates as a data collection and analysis device. A separate computer system controller 141 serves as a controller for controlling operation of the generation laser 24, the detection laser 26, the interferometer 28, and the multiplexing and demultiplexing elements 126. The system controller 141 includes input/output circuits not only for control purposes but also to allow the separate controller 141 to communicate with either the limit switches and the encoder within the spray booth directly or, preferably, with other computers of the local controllers 129 which monitor these signals.

The encoders within the spray booth are coupled to an assembly line 133 which, in turn, moves carriages 134 which support the automotive body assemblies 136 as illustrated in FIG. 7.

The sensors shown in FIG. 7 may be fixed or contain rotation components to allow the sensors to remain pointed approximately at the normals to the article.

The input/output circuits in the local controllers 129 allow its computer to communicate with the encoder(s) which generates a position signal representative of the position of each carriage 134. Preferably, each encoder is an optical incremental encoder mounted to a return wheel about which a chain drive of the assembly line 133 moves. The local controllers 129 know when to look at the position signals provided by their encoders through the use of their limit switches which generate signal inputs to the input/output circuits of the separate computer in the laser room when the carriages 134 holding the assemblies 136 reach predetermined positions within their sensor stations 130.

The data analysis computer 50 is coupled to a computer 137 which receives data from the data analysis computer 50 so that the computer 137 can locate a surface defect in the film on the body assembly 136. The second computer 137 communicates with the computer 50 over a data link 139 and which is located outside the room 122 to report the thickness which represents the thickness of the film or the substrate as described hereinbelow. There will be one networked data link between all the computers wherever they are located. To communicate among the computers one may install a LAN.

A signal is sent by the system controller 141 through its input/output circuits to the robot controller 138 which, in turn, generates a control signal based on location of the surface defect in the film on the assembly 136. The control signal from the robot controller 138 is used by the robot 140 which is movable to a surface coating position to further coat the surface of the layer of the assembly 136.

Referring now to FIG. 7, there is illustrated a sensor head arch, generally indicated at 142, which includes a plurality of sensor heads 34 mounted on vertically and horizontally extending beams 144 along the path of the automotive assemblies 136 so that measurement readings can be taken at various spots such as spots 146 along the car body assembly 136. These sensors may be fixed as shown or contain rotation components to keep the sensor, either individually or in groups, pointed approximately normal to the article at each inspection point 146.

Referring now to FIG. 8, there is illustrated a top plan view of a plurality of sensor arches such as the sensor arch 142 through which automotive car body assemblies 136 travel within a paint spray booth 148. The laser room 122 contains the generation laser 24, the detection laser 26, the interferometer 28, the multiplexing/demultiplexing elements 126, the computer 50, and the separate computerized system controller 141. Optical fiber bundles 128 transmit multiplexed laser light signals therethrough to either various local controllers 129 and then on to the sensor stations 130 in the booth 148 or directly to the sensor stations 130 themselves.

Figure 11:
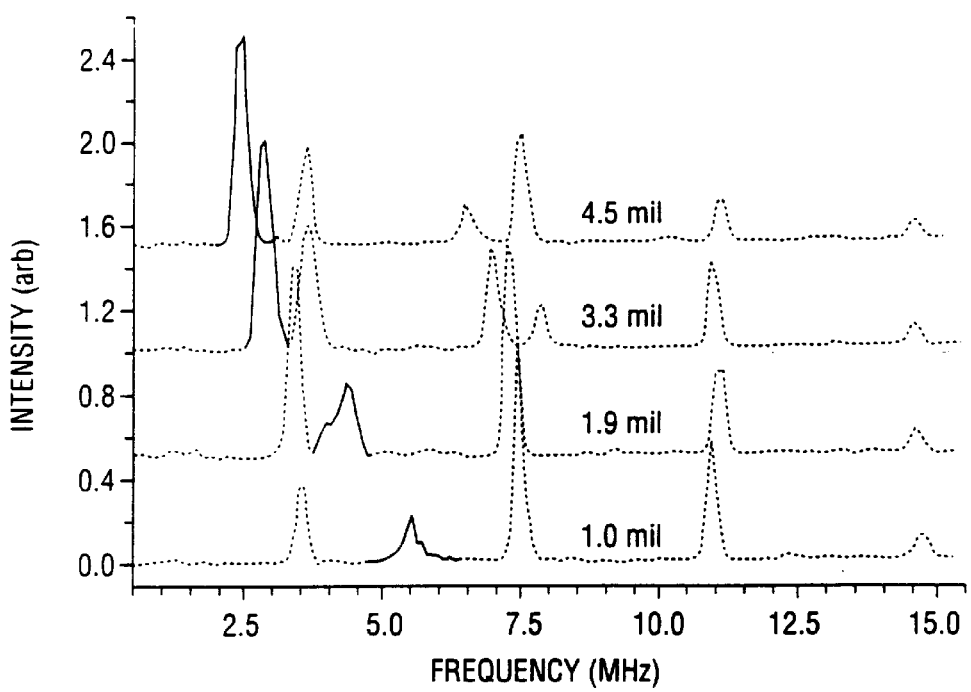
FIG. 11 is a set of graphs, each one of which is similar to the graph of FIG. 10 and illustrating how paint peak resonant frequencies change with varying wet paint thickness.

Referring now to FIG. 11, there is illustrated a set of graphs, each one of which is similar to the graph of FIG. 10 and which illustrate how the resonant paint frequencies change with varying wet paint thickness.

Figure 12:
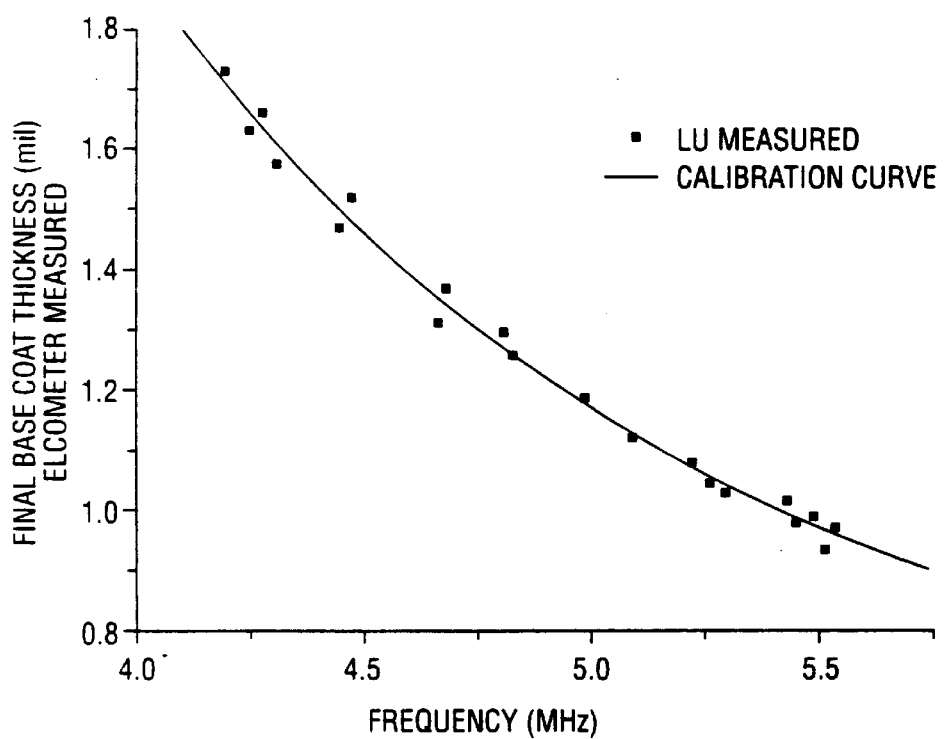
FIG. 12 is a graph illustrating how a calibration curve could be generated from LU measured values of a wet white solvent base coat.

FIG. 12 is a graph illustrating how a curve has been generated from LU measured values of wet white solvent base coat which calibration curve may be stored within the computer 50 for data analysis. Preferably, the data analysis computer 50 passes the resonant frequency signal of FIG. 10, along with previous measurements made on the film or substrate and hence stored in the computer 50, into a model also stored in the computer 50 to determine film build of the film or the substrate on the assembly 136 as described in greater detail hereinbelow.

Summary of Data Analysis In brief, there are three main components to the data analysis of the method and system of the present invention: signal processing; signal modeling; and wet-film to cured-film prediction.

Figure 13:
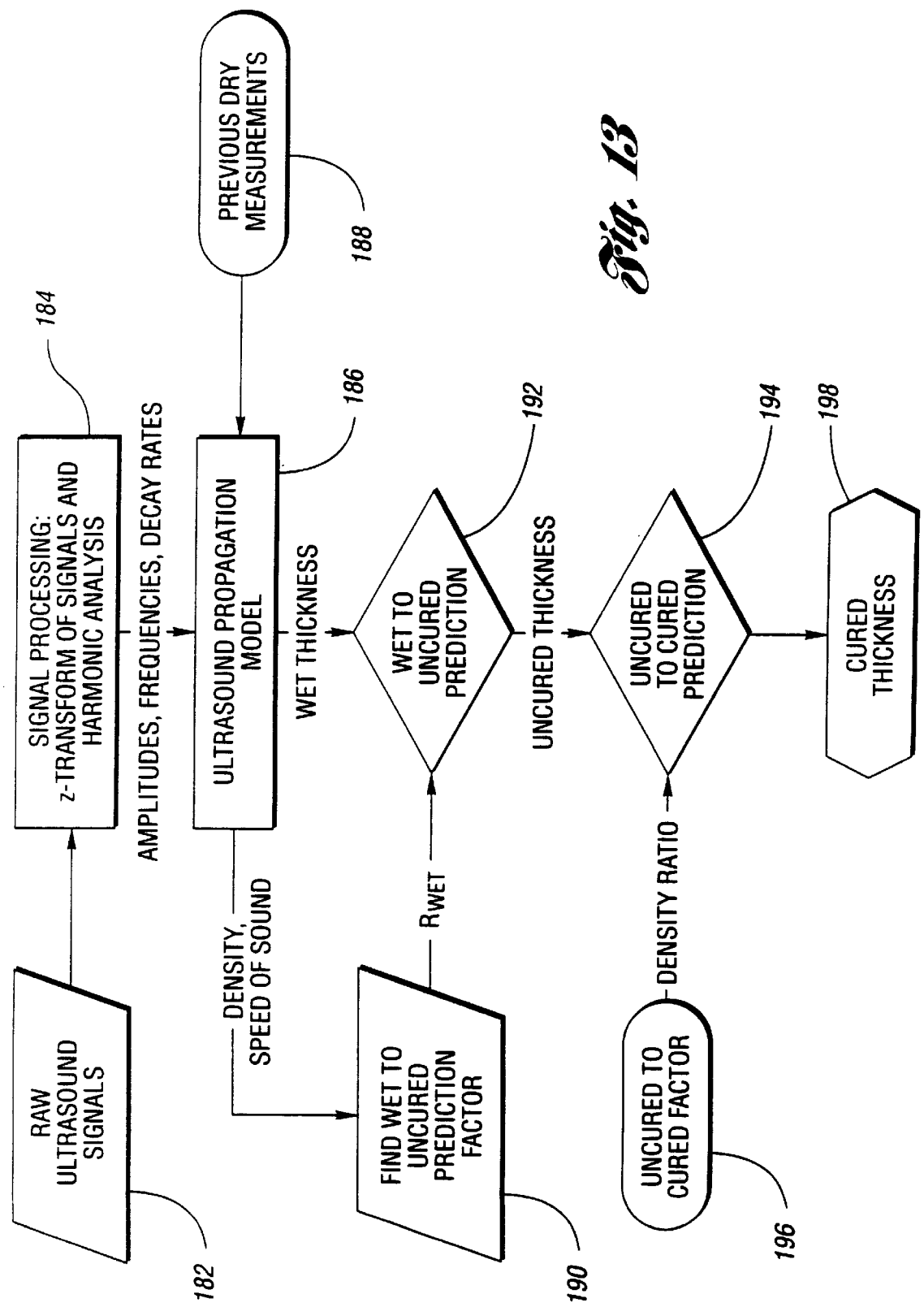
FIG. 13 is a schematic block diagram flow chart illustrating a processing method and system which focuses on how raw ultrasonic signals and/or data are analyzed.

For the particular case of laser-based ultrasonics, the method and system operate in accordance with the block diagram flow chart of FIG. 13.

The flow chart of FIG. 13 is an example of the process involved in a wet paint measurement. Briefly, the programmed computers 50 and 137 transform the raw ultrasound signals or data at block 182 from the interferometer 28 into amplitudes, frequencies, and decay rates after processing at block 184. The frequencies measured are used in a model (physical model or calibration model) to yield a thickness measurement as indicated at block 186.

In the case of automotive coatings, one assumes the measurement of multiple plane-layered systems. The layers can be described as:

Substrate layer: usually steel, aluminum, plastic, or composite

Static film layer: usually cured paint, primer, e-coat, clearcoat, phosphate

Dynamic film layer: usually wet or dehydrated paint, primer, clearcoat, e-coat, etc. Thickness and other physical properties, changing with time.

The method and system can be utilized to measure static and dynamic films There are several methods by which one can convert frequency to thickness. One can use empirical calibration to convert frequency to dried film thickness. The main disadvantages to calibrating dynamic films are the inclusion of extra variables. Some of these would be:

elapsed time of measurement from time of spray
temperature
humidity
preparation of paint
atomization pressure
fan patterning
paint composition These effects may be impossible to quantify accurately.

In essence, a film loses base material via evaporation. The method and system of the present invention measure the amount of base and the amount of solids at the instant of measurement. The method and system have no need to include any of the aforementioned environmental variables that affect the wet film.

Signal Processing of Block 184

The invention models ultrasound as the summation of M decaying sinusoids. The modeling process is: find frequencies and decay rates from raw data; and perform harmonic analysis of raw data using these results.

Find Frequencies and Decay Rates From Raw Data

One measures frequencies and decay rates from raw ultrasound data or signals by pole-zero modeling. Specifically, the ultrasound signals one receives can be modeled as exponentially decaying sinusoids. This problem was first solved by Prony in 1795, and the basic mathematics are substantially identical to what one uses today. Only the computation of the math is modernized. Basically, a decaying complex sinusoid forms a pole in the Z-transform domain. However, only frequency and decay rate information are contained in that pole as discussed by Oppenheim and Schafer in their book "Discrete-Time Signal Processing", Prentice Hall, 1989:

$$y(n) = Ae^{(-\alpha + j2\pi f)n} u[n] \Leftrightarrow A(1 - e^{(-\alpha + j2\pi f)} z^{-1})^{-1}$$

where A is the amplitude of the signal, $\alpha$ is the decay rate, f is frequency, and n is the discrete-time index.

By converting the problem of finding poles to a problem of finding zeros, the algorithm becomes:

Least-squares fit a linear prediction filter to the poles from raw data, i.e. transform signal to z-domain.

Find the zeros of the above filter in the z-domain.

Convert zeros to frequencies and decay rates.

Where:

L=size (order) of filter;

M=number of decaying sinusoidal signals in the raw data-in general M<L; and

N=number of raw data points to transform.

a. Least Squares Fit A Linear Prediction Filter to the Poles From Raw Data

From Prony's method, one solves the following equations to find the filter:

$$A = \begin{bmatrix} y*(1) & y*(2) & \ldots & y*(L) \\ y*(2) & y*(3) & \ldots & y*(L+1) \\ \vdots & \vdots & & \vdots \\ y*(N-L) & y*(N-L+1) & \ldots & y*(N-1) \end{bmatrix}$$

$$B = [b(1), b(2), \ldots, b(L)]^T$$

A b=h h=$[-y*(0), -y*(1), \ldots, -y*(N-L-1)]^T$

L=size of filter

N=number of raw data points to transform y* is the complex conjugate of the data.

The above equation is very difficult to solve not only because of noisiness in y, but also because L>M. Essentially, two (or more) rows in the matrix can become equal and cause a zero to appear in a denominator—one says that the problem is poorly conditioned or ill-conditioned.

In laser ultrasonics of the present invention, the SNR ranges approximately from 0 to 40 dB, i.e. low to moderate SNR. More importantly, the number of sinusoids dynamically changes with the film layer system being measured. Therefore, one needs a robust method to extract the filter from the noisy data.

The SVD, or Singular Value Decomposition method, works quite well on the above equations given the data laser ultrasound produces. The SVD method, as applied to the decaying sinusoid problem, was first described by Kumaresan and Tufts in 1983 and is often called the KT method.

Basically, one solves the filter equation using SVD. With SVD, one can use a filter whose order is larger than the number of signals one expects to receive. Increasing the filter size causes A to become singular. An intermediate solution then truncates the final solution to approximate the number of signals. This improves the accuracy of the fit to the pole locations.

Presently, however, there is no need to truncate the SVD to obtain desired results for frequency precision. Truncation often destroyed the detectability of important signals (like low amplitude metal signals). Instead, "important" or desired signals are identified by amplitudes and knowledge of the film layer system.

b. Find The Poles of the Filter

The zeros of B(x) contain M signal zeros and L–M extraneous (or noise) zeros. The frequency/decay-rate information is extracted by rooting the filter polynomial B(x). For example, consider a one-signal system:

$$B(x) = 1 - e^{(-\alpha + j2\pi f)} x = 0 \Leftrightarrow x = e^{(-\alpha + j2\pi f)}$$

B(z) is changed to B(x) to emphasize that the problem is changed from finding poles to finding zeros. Secondly, the signal zeros will have positive decay rates (for exponentially damped signals) while the noise zeros will have negative decay rates. This is because noise level is theoretically constant (i.e. non-decaying). Finally, for zero decay signals, noise can "push" the measured decay rate to a negative value.

Because of the fairly large order of polynomial, one needs a very robust method of extracting the poles from the filter. Iterative methods are slow and generally fail for large polynomials. An eigenvalue method is used to perform this calculation.

To find eigenvalues of a matrix, one performs the operation:

$$det[W-xI] = 0$$

where det[] is the determinant of the matrix W–xI. The problem is set up using the filter coefficients from B(x) in a companion matrix:

$$B(x) = det[W - xI] = \sum_{i=0}^{L} b(i)x^i = 0$$

$$W = \begin{bmatrix} -\frac{b(L-1)}{b(L)} & -\frac{b(L-2)}{b(L)} & \cdots & -\frac{b(1)}{b(L)} & -\frac{b(0)}{b(L)} \\ 1 & 0 & \cdots & 0 & 0 \\ 0 & 1 & \cdots & 0 & 0 \\ \vdots & \vdots & & \vdots & \vdots \\ 0 & 0 & \cdots & 1 & 0 \end{bmatrix}$$

Then, one can use basically the same theory (and mathematics) involved in SVD to find the eigenvalues of the new matrix. Specifically, a QR method is used to estimate the eigenvalues. Specifics of how to compute the QR decomposition are well known.

c. Convert From Roots To Frequencies And Decay Rates

The signal zeros are sorted from the noise zeros by ignoring all |z|<c where for now c=1.000000. This value may be changed to a number like 0.980000 because sometimes the metal peaks' signal zeros are pushed inside |z|<1 by noise (these generally lie at about 0.9995 or 0.995).

To determine frequency f and decay α, one uses the following:

$$f = a \, \tan(z_i/zr)/2\pi$$

$$\alpha = -\log(|z|)$$

Perform Harmnonic Analysis of Block 184

In order to obtain Amplitudes, one simply performs a harmonic data analysis using the frequencies and decay rates obtained above. Essentially, one performs a general linear least squares fit to the raw data:

$$K = \begin{bmatrix} \exp(s_1 0) & \exp(s_2 0) & \cdots & \exp(s_L 0) \\ \exp(s_1 1) & \exp(s_2 1) & \cdots & \exp(s_L 1) \\ \vdots & \vdots & & \vdots \\ \exp(s_1(N-1)) & \exp(s_2(N-1)) & \cdots & \exp(s_L(N-1)) \end{bmatrix}$$

$$Ka = y$$

$$a = [a_1, a_2, \ldots, a_L]^T$$

$$y = [y(0), y(1), \ldots, y(N-1)]^T.$$

These equations are not ill-conditioned and are thus easy to solve by general linear least squares. Specifically, a simple Gauss-Jordan technique is used to invert K. This technique is also very well known and specifics of computation will not be discussed further.

Signal Modeling of Block 186

Modeling of the propagation of ultrasound in the layers is important to any non-calibrating measurement, as described herein. The system is modeled as a compressional wave traversing through plane layers.

Given enough information (i.e. from block 188) and enough signal (i.e. from block 184), one can find (true) wet thickness. Additionally, one can find speed of sound, density, and possibly viscosity and attenuation. The acoustic impedance of a material is the product of speed of sound and density:

$$Z = \rho c$$

Acoustic impedance controls how a wave is transmitted/reflected at a boundary (i.e. free, rigid, or other reflection) and how the "paint" frequencies interact with "metal" frequencies (and vice versa). Thickness and speed of sound determine how quickly the wave propagates through a layer. Attenuation describes how much energy the wave loses (to heat or other) as it propagates through the layer. Given the model of block 186, as well as good data from block 184, one can solve for any of speed of sound, thickness, density, and/or attenuation using optimization techniques.

The resonance frequency model of block 186 is used to obtain thickness, speed of sound, and density information. Consider a lossless single layer film on a lossless steel substrate. The model for frequency resonance for this particular system is:

$$z_p \tan\left(2\pi f \frac{d_p}{c_p}\right) + z_s \tan\left(2\pi f \frac{d_s}{c_s}\right) 0 = 0 = Q(d, c, \rho, f)$$

where f is any resonant frequency (paint or metal), d is thickness, c is speed of sound, subscript p refers to paint layer qualities, and subscript s refers to steel substrate qualities.

This equation can be solved numerically. Specifically, one minimizes Q(d,c,ρ,f) for desired variables/parameters/data. However, there are many ways to perform the minimization. For example, since one knows the various properties of the steel, one minimizes the following:

$$\frac{z_p}{Z_s}\tan\left(2\pi f_i \frac{d_p}{c_p}\right) + \tan\left(2\pi f_i \frac{d_s}{c_s}\right) = Q\left(f_i; z_p, \frac{d_p}{c_p}\right)/Z_s$$

$$\text{Min}_{simplex}\left\|\sum_i Q^2\left(f_i; z_p, \frac{d_p}{c_p}\right)/Z_s^2\right\| \Rightarrow z_{opt}, (d/c)_{opt}$$

where i=1, 2, . . . number of measured resonances. The ; symbol represents that z and d/c are parameters to be optimized while $f_i$ is input data. The minimization is performed using the well known simplex method, and will not be discussed in detail here.

Wet Prediction

The process to predict a cured film thickness from a wet film thickness is a two-step process:

Perform wet to uncured prediction of block 192;
  estimate wet to uncured prediction factor from data of block 190;
  calculate uncured thickness; and
Perform uncured to baked or cured prediction of block 194.

Perform Wet to Uncured Prediction (Block 192)

Estimate Wet to Uncured Prediction Factor Via Laser-Based Ultrasound (Block 190)

Solving for the quantities such as z and d/c in the wet layer is important. For the particular case of ultrasonic measurement, one measures impedance and one-way transit time of the wet layer—call them $Z_{wet}$, $(d/c)_{wet}$, respectively. Density and speed of sound vary with particulate size and particulate concentration, as well as solvent properties. If one can measure impedance, one can then estimate percent solids or particulate concentration—call percent solids $R_{wet}$ (let $R_{wet}$ be a pure ratio less than 1 and not a percent). Symbolically, one measures $R_{wet}$ (or $(Rv)_{wet}$) from $Z_{wet}$ as:

$$R_{wet}\, V_{wet=}(Rv)_{wet}=f(i\, Z_{wet}).$$

One can also use this data to measure $d_{wet}$.

The functionality of f( ) is either derived or measured, depending on application, knowledge available, etc. Note that it is very possible to measure f( ) using results from other techniques, say Time Resolved Infrared radiometry (TRIR), as well as using this same process for wet prediction. See the next section for details.

Calculate Uncured Thickness (Block 192)

Once $R_{wet}$ and $d_{wet}$ (or even $(Rv)_{wet}$ and $(d/v)_{wet}$ for the special case of this laser ultrasonic application) are estimated, one is ready to perform wet prediction. The following wet film to dry film thickness prediction conversion is independent of measurement method.

Percent solids or particulate concentration tells what the wet layer will reduce to if all of the solvent is removed. The predictive thickness of the uncured but base-free paint is called $d_{uncured}$. Mathematically, this is expressed as:

$$d_{uncured}=R_{wet}\, d_{wet}$$

or $$d_{uncured}=(Rv)_{wet}(d/v)_{wet}.$$

As an example, if one measures 4 mils thick wet water-based (=$d_{wet}$=4.00 mil) at 75% solids (=$R_{wet}$=0.75), that means the wet layer will reduce to 3 mils (=$d_{uncured}$= $R_{wet}d_{wet}$=0.75×4.00 mil=3.00 mil).

Perform Uncured to Baked (Le. Cured) Prediction (Block 194)

One must also know how the uncured wet layer chemically reacts to become "paint". However, there is basically no way to predict how wet paint chemically reacts via ultrasound, thermal, image interferometry, microwave, millimeter wave, capacitance, etc., unless the reaction itself is monitored.

One measures the prediction in a laboratory or through knowledge of the chemical reaction. One method used with the present invention is to measure the prediction using density, as indicated at block 196. The density of cured paint will be measured—call it $\rho_{cured}$. The density of uncured (and solvent- or water-free) paint will be measured—call it $\rho_{uncured}$. Because the paint has been applied to a surface, the area of the uncured and cured paint is constant. Therefore, the uncured to cured paint prediction is:

$$d_{cured}\, \rho_{cured}=d_{uncured}\, \rho_{uncured}.$$

One can then predict the final, baked or cured thickness, as indicated at block 198.

It is possible that the above method can be used to measure wet glue to dry glue thickness, as well as other properties of the glue. Molten coatings, certain composites, etc. would also be measurable with the method and system of the present invention.

Wet Film Prediction and Measurement

Determination of the Functionality of $R_{wet}$

There are several ways to determine the functionality of $R_{wet}$. First is to use theory of the basic measurement technique. For example, one could incorporate particle size, particle composition, particle concentration, base composition, particle-base interaction, frequency, etc. into a physical model for f( ).

Another method to determine the functionality of $R_{wet}$=f( ) for a given paint is calibration. As an example, consider measurement of $R_{wet}$=f($c_{wet}$) for black solvent-based paint. One can prepare many samples of paint with various $R_{wet}$ and measure the corresponding $c_{wet}$. Then a curve can be fit in order to determine $R_{wet}$=f($c_{wet}$).

While the best mode for carrying out the invention has been described in detail, those familiar with the art to which this invention relates will recognize various alternative designs and embodiments for practicing the invention as defined by the following claims.

What is claimed is:

1. A method for measuring a physical parameter of at least one layer of a multilayer article without damaging the article, the method comprising the steps of:
  generating a first pulse of electromagnetic energy;
  transmitting the first pulse to a sensing station;
  generating a second pulse of electromagnetic energy;
  transmitting the second pulse to the sensing station;
  directing the first pulse at the sensing station toward a first spot on a surface of the article to generate an ultrasonic wave in the article which, in turn, causes ultrasonic motion of the surface of the article without damaging the article;
  directing the second pulse at the sensing station toward a second spot on the surface of the article which substantially overlaps the first spot to obtain a reflected pulse of electromagnetic energy which is modulated based on the ultrasonic motion of the surface;
  transmitting the reflected pulse from the sensing station;
  detecting the reflected pulse after the step of transmitting the reflected pulse to obtain a corresponding ultrasonic electrical signal; and processing the ultrasonic electrical signal to obtain a physical parameter signal which represents the physical parameter of the at least one layer at the first and second substantially overlapping spots.

2. The method as claimed in claim 1 wherein the step of processing includes the step of initially processing the ultrasonic electrical signal to obtain at least one resonance frequency signal based on resonance of the at least one layer and then processing the at least one resonance frequency signal to obtain the physical parameter signal.

3. The method as claimed in claim 1 wherein the article includes a metal substrate layer.

4. The method as claimed in claim 1 wherein the article includes a plastic substrate layer.

5. The method as claimed in claim 1 wherein the article is a vehicle body.

6. The method as claimed in claim 1 wherein the at least one layer is a solid film.

7. The method as claimed in claim 1 wherein the at least one layer is a liquid film.

8. The method as claimed in claim 1 wherein the physical parameter is thickness of the at least one layer.

9. The method as claimed in claim 1 wherein the ultrasonic wave is a longitudinal ultrasonic wave.

10. The method as claimed in claim 1 wherein the steps of generating the first and second pulses and the step of detecting the reflected pulse are performed at a location remote from the sensing station.

11. The method as claimed in claim 1 wherein the first and second pulses are substantially collinear at the first and second overlapping spots.

12. The method as claimed in claim 2 wherein the step of initially processing the ultrasonic electrical signal includes the steps of digitizing the ultrasonic electrical signal to obtain a digitized ultrasonic electrical signal and applying a Z-transform to the digitized ultrasonic electrical signal.

13. The method as claimed in claim 1 wherein the sensing station is located in a hazardous environment and wherein the steps of generating the first and second pulses and the steps of detecting the reflected pulse and processing the ultrasonic electrical signal are performed outside of the hazardous environment.

14. The method as claimed in claim 1 further comprising the step of moving the article at the sensing station relative to the first and second pulses during the steps of directing the first and second pulses.

15. The method as claimed in claim 14 further comprising the steps of generating a position signal representative of the position of the article relative to the sensor station and wherein the physical parameter signal is processed with the position signal to locate a defect in the article.

16. A system for measuring a physical parameter of at least one layer of a multilayer article without damaging the article, the system comprising:

a generation laser for generating a first pulse of electromagnetic energy;

a first optical fiber for transmitting the first pulse therethrough to a sensing station;

a detection laser for generating a second pulse of electromagnetic energy;

a second optical fiber for transmitting the second pulse therethrough to the sensing station;

a sensor head coupled to the first and second optical fibers at the sensing station and having at least one optical component for directing the first pulse transmitted through the first optical fiber toward a first spot on a surface of the article to generate an ultrasonic wave in the article which, in turn, causes ultrasonic motion of the surface of the article without damaging the article, the sensor head also having at least one optical component for directing the second pulse toward a second spot on the surface of the article which substantially overlaps the first spot to obtain a reflected pulse of electromagnetic energy which is modulated based on the ultrasonic motion of the surface, the sensor head receiving the reflected pulse;

an optical detector coupled to the sensor head for detecting the reflected pulse to obtain a corresponding ultrasonic electrical signal; and a signal processor for processing the ultrasonic electrical signal to obtain a physical parameter signal which represents the physical parameter of the at least one layer at the first and second overlapping spots.

17. The system as claimed in claim 16 wherein the signal processor processes the ultrasonic electrical signal to obtain a resonance frequency signal based on resonance of the at least one layer and processes the resonance frequency signal to obtain the physical parameter signal.

18. The system as claimed in claim 16 wherein the optical detector includes an optical interferometer.

19. The system as claimed in claim 18 wherein the optical interferometer is a confocal Fabry-Perot type interferometer.

20. The system as claimed in claim 16 wherein the article includes a metal substrate layer.

21. The system as claimed in claim 16 wherein the article includes a plastic substrate layer.

22. The system as claimed in claim 16 wherein the article is a vehicle body.

23. The system as claimed in claim 16 wherein the physical parameter is thickness of the at least one layer.

24. The system as claimed in claim 16 wherein the ultrasonic wave is a longitudinal ultrasonic wave.

25. The system as claimed in claim 16 wherein the lasers and the optical detector are located remote from the sensing station.

26. The system as claimed in claim 16 wherein the at least one layer is a solid film.

27. The system as claimed in claim 16 wherein the at least one layer is a liquid film.

28. The system as claimed in claim 16 wherein the first and second pulses are substantially collinear at the first and second overlapping spots.

29. The system as claimed in claim 16 wherein the signal processor initially processes the ultrasonic electrical signal by digitizing the ultrasonic electrical signal to obtain a digitized ultrasonic electrical signal and then by applying a Z-transform to the digitized ultrasonic electrical signal.

30. The system as claimed in claim 16 wherein the sensing station is located in a hazardous or remote environment and wherein the lasers, optical detector and the signal processor are located outside of the hazardous or remote environment.

31. The method as claimed in claim 16 further comprising means for moving the article at the sensing station relative to the first and second pulses.

32. The system as claimed in claim 31 further comprising a sensor coupled to the means for moving and the signal processor to generate a position signal representative of position of the article relative to the sensor station and wherein the physical parameter signal is processed with the position signal by the signal processor to locate a defect in the article.

33. The system as claimed in claim 32 further comprising a controller coupled to the signal processor for generating a control signal based on location of the defect in the article.

34. The system as claimed in claim 33 further comprising a surface coating mechanism for coating the surface of the article as a function of the control signal.

35. The system as claimed in claim 34 wherein the mechanism includes a robot and wherein the controller is a robot controller.

36. A sensor head adapted for use in a system for measuring a physical parameter of at least one layer of a multilayer article without damaging the article, the sensor head comprising:
- a housing adapted to receive first and second pulse of electromagnetic energy;
- a dichroic beam splitter supported within the housing for transmitting one of the pulses and reflecting the other pulse; and
- a set of optical components supported within the housing for: (1) directing the first pulse toward a first spot on a surface of the article; (2) directing the second pulse toward a second spot on the surface of the article which substantially overlaps the first spot to obtain a reflected pulse of electromagnetic energy; and (3) receiving the reflected pulse.

37. The sensor head as claimed in claim 36 wherein the beam splitter and the set of optical components are supported within the housing so that the first and second pulses are substantially collinear at the first and second overlapping spots.

38. A method for measuring a physical parameter of at least one layer over an extended area of a multilayer article without damaging the article, the method comprising the steps of:
- generating a first pulse of electromagnetic energy;
- directing the first pulse into a first plurality of beams;
- transmitting the first plurality of beams to a plurality of separate locations at a sensing station;
- generating a second pulse of electromagnetic energy;
- directing the second pulse into a second plurality of beams;
- transmitting the second plurality of beams to the plurality of locations at the sensing station;
- directing the first plurality of beams at the locations at the sensing station toward a first plurality of spots on a surface of the article to generate ultrasonic waves in the article which, in turn, causes ultrasonic motion of the surface of the article without damaging the article;
- directing the second plurality of beams at the locations at the sensing station toward a second plurality of spots on the surface the article, each of the second plurality of spots substantially overlapping one of the first plurality of spots to obtain a reflected pulse of electromagnetic energy which is modulated based on the ultrasonic motion of the surface at its respective first and second overlapping spots;
- transmitting the reflected pulses from the sensing station;
- collecting the transmitted reflected pulses to obtain collected pulses;
- detecting the collected pulses to obtain a plurality of corresponding ultrasonic electrical signals; and
- processing the plurality of ultrasonic electrical signals to obtain a plurality of physical parameter signals which represents the physical parameter of the at least one layer over the extended area of the article.

39. The method as claimed in claim 38 further comprising the steps of moving the article relative to the sensor station and generating a position signal representative of the position of the article at the sensor station and wherein the physical parameter signals are processed with the position signal to locate a defect in the extended area of the article.

40. The method of claim 39 further comprising the step of generating a control signal based on location of the defect.

41. The method of claim 40 further comprising the step of coating the surface of the article as a function of the control signal.

42. A system for measuring a physical parameter of at least one layer over an extended area of a multilayer article without damaging the article, the system comprising:
- a generation laser for generating a first pulse of electromagnetic energy;
- a first device for directing the first pulse into a first plurality of beams;
- a first plurality of optical fibers for transmitting the first plurality of beams therethrough to a corresponding plurality of locations at a sensing station;
- a detection laser for generating a second pulse of electromagnetic energy;
- a second device for directing the second pulse into a second plurality of beams;
- a second plurality of optical fibers for transmitting the second plurality of beams therethrough to the corresponding plurality of locations at the sensing station;
- a plurality of sensor heads, each of the sensor heads positioned at one of the locations at the sensing station and coupled to one of each of the first and second pluralities of optical fibers, each of the sensor heads having at least one optical component for directing one of the first plurality of beams toward one of a first plurality of spots on a surface of the article to generate an ultrasonic wave in the article which, in turn, causes ultrasonic motion of the surface of the article without damaging the article, each of the sensor heads also having at least one optical component for directing one of the second plurality of beams toward one of a second plurality of spots on the surface of the article which substantially overlaps its corresponding spot of the first plurality of spots to obtain a reflected pulse of electromagnetic energy which is modulated based on the ultrasonic motion of the surface at its respective first and second overlapping spots, each of the sensor heads also receiving its reflected pulse;
- a third device coupled to each of the sensor heads for collecting the reflected pulses to obtain collected pulses;
- an optical detector coupled to the third device for detecting the collected pulses to obtain a plurality of corresponding ultrasonic electrical signals; and
- a signal processor for processing the plurality of ultrasonic electrical signals to obtain physical parameter signals which represents the physical parameter of the at least one layer over the extended area on the article.

43. The system as claimed in claim 42 further comprising a mechanism for moving the article relative to the sensor station and a sensor coupled to the mechanism and the signal processor to generate a position signal representative of position of the article relative to the sensor station and wherein the physical parameter signals are processed with the position signal by the signal processor to locate a defect in the article at the extended area of the article.

44. The system as claimed in claim 43 further comprising a controller coupled to the signal processor for generating a control signal based on location of the defect in the article.

45. The system as claimed in claim 44 further comprising a surface coating mechanism for coating the surface of the article as a function of the control signal.

46. The system as claimed in claim 45 wherein the mechanism includes a robot and the controller is a robot controller.

47. The system as claimed in claim 42 wherein the second plurality of optical fibers couple the sensor heads to the third device.

48. The system as claimed in claim 42 further comprising a third plurality of optical fibers for coupling the sensor heads to the third device.

* * * * *